(12) United States Patent
Stock et al.

(10) Patent No.: US 8,477,320 B2
(45) Date of Patent: Jul. 2, 2013

(54) METHOD AND MEASURING ARRANGEMENT FOR THE THREE-DIMENSIONAL MEASUREMENT OF AN OBJECT

(75) Inventors: Karl Stock, Ellwangen (DE); Michael Zint, Ulm (DE); Rainer Graser, Ulm (DE); Raimund Hibst, Erbach (DE)

(73) Assignee: Degudent GmbH, Hanau (DE)

( * ) Notice: Subject to any disclaimer, the term of this patent is extended or adjusted under 35 U.S.C. 154(b) by 0 days.

(21) Appl. No.: 13/320,576

(22) PCT Filed: May 17, 2010

(86) PCT No.: PCT/EP2010/056755
§ 371 (c)(1),
(2), (4) Date: Jan. 5, 2012

(87) PCT Pub. No.: WO2010/130843
PCT Pub. Date: Nov. 18, 2010

(65) Prior Publication Data
US 2012/0156636 A1 Jun. 21, 2012

(30) Foreign Application Priority Data
May 15, 2009 (DE) .......................... 10 2009 025 815

(51) Int. Cl.
*G01B 11/24* (2006.01)
(52) U.S. Cl.
USPC .......................................... 356/601; 356/609

(58) Field of Classification Search
USPC ............ 356/600–624; 250/201.8, 200, 201.1, 250/216, 203.1–203.2; 359/385, 362, 368; 362/574, 551, 572; 600/160, 425, 101, 300
See application file for complete search history.

(56) References Cited

U.S. PATENT DOCUMENTS

| | | | |
|---|---|---|---|
| 5,165,063 A | 11/1992 | Strater et al. | |
| 2002/0027708 A1 | 3/2002 | Lin et al. | |
| 2007/0053204 A1 | 3/2007 | Krohne et al. | |
| 2010/0099984 A1 | 4/2010 | Graser | |

FOREIGN PATENT DOCUMENTS

| | | |
|---|---|---|
| DE | 103 21 885 | 12/2004 |
| DE | 10 2006 007 172 | 8/2007 |
| EP | 0 466 979 | 1/1992 |
| EP | 1 398 597 | 3/2004 |
| WO | WO 2007/051567 | 5/2007 |
| WO | WO 2007/090865 | 8/2007 |

*Primary Examiner* — Tri T Ton
(74) *Attorney, Agent, or Firm* — Ladas & Parry, LLP

(57) ABSTRACT

Method for measuring the shape of a section of a semi-transparent object such as one section of a tooth, using a light source for generating light with a broadband spectrum in a device for generating a multifocal illumination pattern, a lens with a large chromatic aberration for imaging foci of the illumination pattern onto the object, and a detection device for determining the wavelength spectra of the foci confocally imaged onto the object via the lens, wherein a spectral peak position of each focus is determined from the respective wavelength spectrum, from which position the extent of the object in the direction of the imaging beam (Z coordinate) is calculated.

43 Claims, 1 Drawing Sheet

Example of lay-out

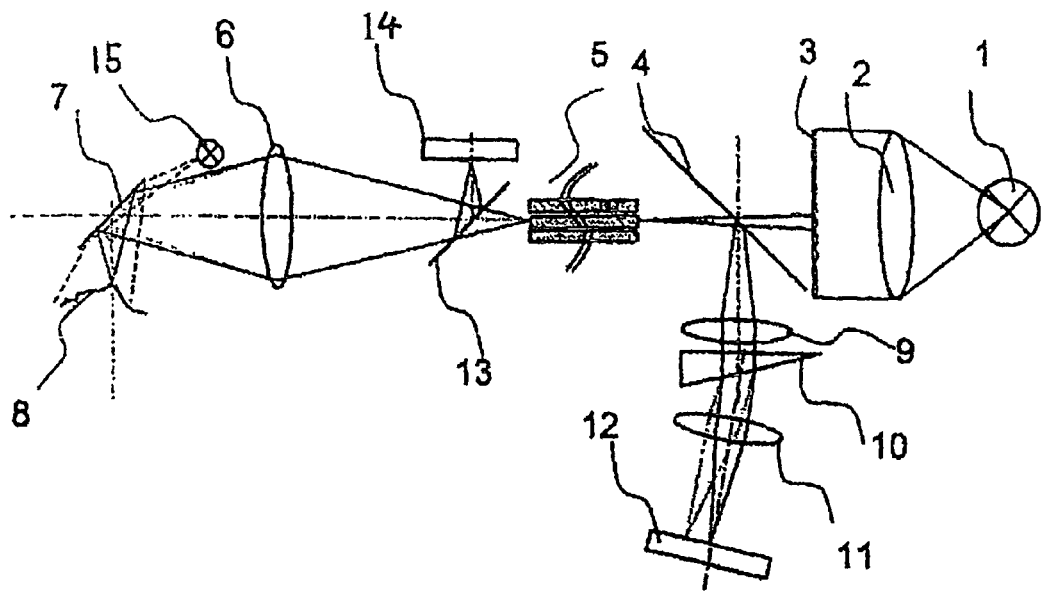
Fig 1: Example of lay-out
Fig.2: a) Example of arrangement of light guides on illumination or detection side. b) Example of arrangement of light guides on test sample side
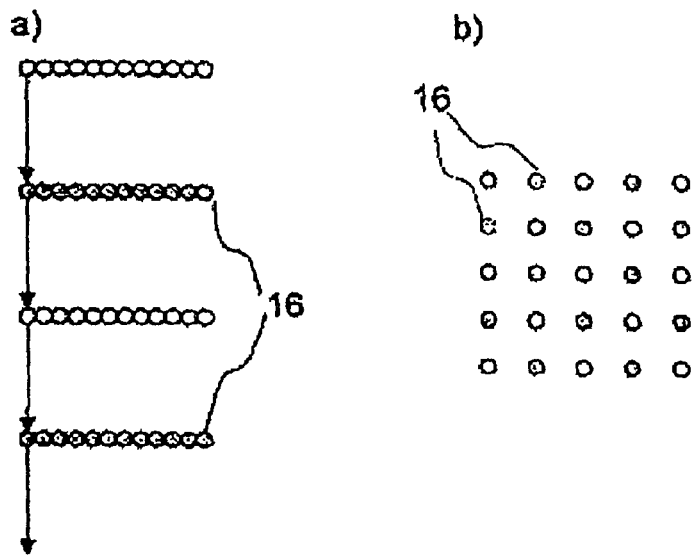

METHOD AND MEASURING ARRANGEMENT FOR THE THREE-DIMENSIONAL MEASUREMENT OF AN OBJECT

This application is a 371 of PCT/EP2010/056755, filed on May 17, 2010, which claims priority to German Patent Application No. 10 2009 025 815.9, filed May 15, 2009, both of which are incorporated herein by reference.

The invention relates to a method for measuring the shape of at least a section of an object, in particular a semi-transparent object such as at least a section of a tooth, using a light source to generate light with a preferably broadband spectrum, a device to generate a multi-focus illumination pattern, an objective lens with high chromatic aberration to image the foci of the illumination pattern onto the object, a detector device to acquire the wavelength spectrum of the foci imaged confocally onto the object by the objective lens, whereby the spectral peak position of each peak is determined from the respective wavelength spectrum and is used to compute the extent of the object along the direction of the imaging ray (z coordinate), whereby the multi-focal illumination pattern is generated by light guides arranged between the light source and the objective lens with high chromatic aberration, whereby the objective lens images the ends of the light guides on the object side onto the object and images light returned from the object onto the ends of the light guides on the object side, and whereby returned light is guided by the light guides onto the detector device.

The invention further relates to a measuring system for three-dimensional measuring of at least part of an object, in particular of a semi-transparent object such as a tooth or section thereof, comprising a light source with a continuous, in particular wide-band spectrum, a device to generate a multi-focus illumination pattern, an objective lens with high chromatic aberration to image foci of the illumination pattern onto the object, a detector unit with a camera chip to determine the wavelength spectra of the foci imaged by the objective lens, as well as a spectrum-dispersing device, onto which light returned from the object can be imaged by the objective lens, whereby between the light source and the objective lens are arranged light guides, which produce the illumination pattern and possess ends on the object-facing side that are arranged in an imaging plane or range of imaging planes, of the objective lens, whereby between the ends of the light guides on the illumination side and the detector device is arranged a redirection device to redirect the light that is emerging from the light guide and has been returned from the object.

In many technical fields one is faced with the task of measuring the three-dimensional shape of bodies. An example of this is the need to determine the shape of a tooth, which is required in the manufacture of a dental prosthesis. For this, all methods are of advantage that eliminate the need of taking a plaster cast. The literature contains a series of methods for determining the three-dimensional shape of bodies. Optical methods deserving mention are in particular the structured-light scanning method or phase shift method, optical coherence tomography, and holography. A commercially available system for the intraoral determination of tooth shapes is based on the phase shift method.

In particular on less cooperative bodies, as teeth can be considered as due to their high volume scattering, the mentioned methods often fail. For example, in the structured-light scanning methods, dispersion can lead to blurring of the strips, which reduces resolution.

Alternatively, one uses a suitable objective lens with a highly wavelength-dependent focal length for the imaging of the focus or foci of a wideband-spectrum light source. As a result, depending on their wavelength, the foci will be imaged in focus at different distances from the objective lens. After the foci have been re-imaged into the pinhole or pinhole array by the objective lens, an intensity maximum is detected for the particular wavelength that is imaged in focus at this particular sample distance. Thus, by determining the spectral peak position, one is able to determine the distance of the sample to the objective lens at this point, and ultimately the three-dimensional shape of the body. The evaluation is performed point-by-point using a spectrometer or line-by-line using a line spectrometer with camera chip. In particular the multi-focus arrangement, preferably in combination with a micro-lens array and a matched pinhole array, is a promising option on account of the low expected time requirements for image recording.

DE-A-10 2006 007 172, WO-A-2007/090865, and DE-A-10 2007 019 267 describe different arrangements based on this principle. All of these have in common, that all components are integrated into one device. The option of feeding the light source via light guides is only described in DE-A-10 2007 019 267. In particular for measurements of a tooth, where on the one hand the available (mouth) space is limited and the dentist must guide the device manually, a most compact and lightweight handheld unit with as few components as possible is desirable. A further drawback of the described lay-outs is the fixed assignment of the micro-lens and pinhole pattern on the one side and the distribution of the measurement points on the sample side, which represents a compromise between an optimum measuring point distribution on the sample and the distribution of spectra on the camera chip.

Known from EP-B-0 321 529 is a measuring arrangement for measuring the distances between an objective lens with high chromatic aberration and an object. Used as detector is a black-and-white white CCD camera, in front of which is arranged a spectrum-dispersing apparatus with an input slit. Thus the wavelength information for each point is converted to location information in order to obtain a profile image of the surface of the object.

EP-B-0 466 979 relates to an arrangement for simultaneous confocal image generation. Light points are generated by a screen aperture such as a Nipkow disk and are then imaged onto an object. A CCD array camera is used as detector unit.

Known from DE-A-102 42 374 is a confocal distance sensor with a projection lens with chromatic aberration, which is intended for inspections in the electronics field. Feasible light sources are those with a multitude of point light sources. Used as light receivers are point detectors, whereby each point detector is assigned to one point light source and the two are arranged confocally with respect to each other.

Known from DE-A-103 21 885 is a confocal measuring arrangement for the three-dimensional measuring of an object with chromatic depth resolution, in which a multitude of foci are generated by means of a micro-lens array and are imaged onto the object. The reflected light is focussed back into the plane of the microlens foci. This arrangement is used to measure two- or three-dimensional micro-profiles of test objects or two- or three-dimensional profiles of reflectivity or transparency.

Objective of the present invention is to further develop a measuring arrangement and a method of the above-mentioned type in such a manner that it becomes possible to perform highly precise measurements with easily set-up measures, whereby an optimum distribution of measuring points on the sample should also allow an optimum spectrum distribution in the detector unit. In addition, a compact, easy-to-handle unit is to be made available for measuring, in particular for intraoral measuring.

To meet this objective, in a measuring set-up of the above-mentioned type the ends of the light guides on the object side are arranged in such a manner that on the object side a measuring point distribution can be imaged that is independent of the distribution of microlenses or pinholes on the illumination or detector side.

With respect to the method, the invention is in principle characterized by the creation of an arrangement of the ends of the light guides (5) on the object side that is different than that of the ends of the light guides on the illumination or detection side so that a distribution of measuring points on the object side will be independent of the distribution of microlenses or pinholes on the illumination or detector side.

The invention's teaching creates the option of separating the evaluation section from the measuring section, since the use of light guides in accordance with the invention provides an interface that is essentially independent of lengths.

This means that the measuring section and the evaluating section can be connected by light guides that end in the individual component groups.

Further, according to the invention one uses a measuring point distribution that does not necessarily have to coincide with the distribution of microlenses or pinholes, which consequently allows an uncomplicated evaluation process.

Thus, the following are essential elements of the measuring set-up according to the invention
- an illumination unit, in which the light of a suitable light source is coupled into the light guides
- an element to separate the illumination beam path from the detection beam path
- a light guide bundle with a suitable spatial arrangement of light guides on the illumination and detection side and a suitable arrangement of light guides on the sample side
- an objective lens with high chromatic aberration to image the light guide ends onto the test object and to image the light returned from the test body onto the light guide ends
- a colour-measuring unit to determine the respective peak positions and thus the distance of the measured point from the objective lens.

This colour-measuring unit preferably consists of a dispersive element to create a spread spectrum from the light of each light guide along a line, and a camera chip, onto which the spread spectra of the measured points are imaged. The arrangement of light guides on the illumination and detection side is chosen to ensure a most efficient coupling-in of the light from the light source on the one hand, and a most efficient spatial utilization of the camera chip on the other. The teaching of the invention allows the use of a large number of light guides and thus makes it possible to measure a large number of measuring points with sufficient spectral accuracy.

The arrangement of light guides in the hand unit, i.e. the test body side, is chosen so that after a subsequent superposition of individual images, one obtains a most advantageous distribution of measuring points on the test body.

If the distance between measuring points is greater than the desired resolution, the illumination pattern is adjusted accordingly. This is accomplished either by a suitable element in the device or by continuously moving the measuring unit, whereby the resulting individual images are superimposed to form a total image in a suitable manner.

In particular it is intended that the light be focussed onto the ends of the light guides on the illumination or detection side in the shape of lines. This results in the returned light being imaged on the detector device in the shape of lines as well, which does not only simplify the analysis but also renders it more precise.

The line-shaped focussing is achieved in particular using cylindrical lenses.

As light sources one can use wide-band light sources such as halogen lamps, xenon lamps, and in particular LEDs, in particular white light LEDs or RGD LEDs. In this, there exists the possibility of illuminating the light guides in a modulated, pulsed, or flashed fashion, which in combination with a detection process that is synchronized to the light source creates the option of achieving an efficient suppression of ambient light effects.

A further option is to use several light sources, which increases the overall amount of light. In this, the spatial arrangement of the individual light sources can be adapted to the spatial arrangement of light guides.

Preferably a colour camera is used as the detector device. Depending on the required measuring accuracy, one uses a single-chip colour camera, a three-chip colour camera, or a colour camera with filter-wheel technology.

In accordance with a suggestion with its own inventive merit it is intended that the light guides on the illumination or detection side be arranged in rows or lines. Subsequently the light guides are quasi-twisted, so that a uniform distribution of light guides is achieved on the sample side. Correct measurements are possible nevertheless, by carrying out a calibration process to assign the position of the individual light guides on the sample side to the ends on the illumination side.

The invention is further characterized by the fact that for background-suppression purposes one uses in each individual measurement only a portion, such as half, of the light guides for the actual measurement, whereas the other, not-illuminated portion is used for measuring the background. The varying of the illumination can for example be achieved either using an LCD modulator or the variable beam offset of a tilting glass plate. In each individual measurement, all of the light guides of any one line are either used for distance measuring or for background measuring.

The invention further intends that the measuring set-up comprises a second light source illuminating the object. The spectral range of the second light source may be outside of the wavelength region of the light source used for the measurements. This allows the option of generating a live image.

For the purpose of generating a live image one also should consider integrating a camera chip with an objective lens. Corresponding components will then be integrated in the part of the measuring set-up that is used for measuring, i.e. usually a hand-held unit that is connected to an evaluating unit via the light guides.

Consequently, the invention relates to a device for measuring the three-dimensional shape of bodies, comprising in particular:
a) a light source to generate light with a wide-band spectrum
b) optics to couple the light into a light-guide bundle
c) a light-guide bundle
d) an objective lens with high chromatic aberration to image the de-coupling ends of the light guides onto the body to be measured and to re-image the light returned from the body into the de-coupling ends of the light guides
e) a colour-measuring unit for the simultaneous recording of the wavelength spectra of all light guides
f) an analysis unit to determine the spectral peak position for each focus, from which ultimately is determined the distance of the respective location from the objective lens and consequently the three-dimensional shape of the body.

The invention further relates to a measuring method that can be carried out using such a device.

Further details, advantages, and features of the invention are not only found in the claims, the characteristic features explained therein—on their own and/or in combination—, but also in the following description of preferred embodiment examples and in particular the following supplementary explanations.

The figures show:

FIG. 1 shows an example of the arrangement of light guides on the illumination or detection side, and FIGS. 2a, 2b show arrangements of light guides.

In the following we shall explain the essential features of the invention using the example of measuring the shape of an object. The example used is that of a tooth, but that shall not place any limits on the teaching of the invention.

Irrespective thereof, the invention expressly refers to the disclosure of the international application WO 2008/129073 (PCT/EP2008/054982) of the applicant. The characteristic features disclosed in said application, in particular with respect to the evaluation of spectra and the arrangement of components required for the measuring process should be considered as disclosed in the present application without the need for any further references in the following.

FIG. 1 shows in an exemplary manner a preferred embodiment for measuring teeth. As white-light source one uses a halogen lamp, whereby the light is collimated by a lens 2.

The collimated light beam is incident onto an arrangement of e.g. 10 cylindrical lenses 3 and subsequently onto a beam splitter 4. Consequently, the transmitted light portion is focussed onto ten lines, where it is coupled into 2000 light guides 5, which are arranged as 200 light guides per line, for example.

The arrangement of light guides 5, or the parts thereof contained in a hand-set, on the test body side can for example correspond to a regular square pattern of 40×50 measuring points with a distance between measuring points of 220 μm and an extent of the measuring field of approximately 8.6 mm×10.8 mm.

The light guide ends are imaged onto the test sample 8 via the objective lens 6 with highly colour-dependent focal length and the beam diverter 7. In this, the ends of the light guides 5 are located in an imaging plane of the objective lens 6 or in a range of imaging planes.

Due to the high chromatic aberration of the objective lens 6, only one particular colour will be imaged in focus at the particular measuring point, in dependence on the distance of the measuring point from the objective lens 6, i.e. only one particular wavelength satisfies the confocality condition. In other words: the imaged object-sided ends of the light guides 5—that are forming foci—comprise light of different wavelengths, whereby at one wavelength the object-sided end is imaged in focus on the object 6, which satisfies the confocality condition. Accordingly, in the return-imaging of the light returned from the surface of the test sample, only the particular spectral component enters the light guide 5 that is imaged in focus, i.e. satisfies the confocality condition.

In this, the chosen object-to-image ratio of the objective lens 6 determines the size of the measuring field and the resolution.

As the density of measuring points increases, the light scattering from the test object 8 increases, and one is faced with an increasing portion of stray light entering the light guides 5, in addition to the peak wavelength, i.e. the wavelength at which the object-sided end of the light guide is imaged in focus. However, the resulting increase of the white light portion impedes the determination of the spectral peak position. A white light portion of 1% already renders a practical determination of the peak position using a colour camera impossible. For this reason, one chooses in accordance with the invention a spectrometric lay-out in which the light emerging from the light guides 5 is imaged onto a camera chip 12 via the beam splitter 4 and the optical elements 9 and 11, while a prism 10 effects a spectral dispersion of the light. The prism 10 is arranged between the optical elements 9 and 11. This results in a set-up equal to the one disclosed in WO 2008/129073. As already mentioned, this disclosure is expressly being referred to and is to be taken as disclosed in the present application.

According to the corresponding set-up, each light guide end is imaged onto a line on the camera chip 1, whereby the position along this line is correlated to a certain wavelength, as is the case in a conventional line spectrometer. The distance between the ten lines, each consisting of 200 light guides 5, is chosen so that the light from each light guide 5 that is reflected at the beam splitter 4 and is incident upon the camera chip 12 is spectrally dispersed along a distance of approximately 100 pixels without overlap to the next line. Thus, in a camera chip with 1024 pixels by 1024 pixels a strip of approximately 5 pixels by 100 pixels is available for spectral dispersion for each measuring point, i.e. for each light guide.

After an image has been recorded, analysis of the image information or measured data will take place either on the camera chip 12 or in an external unit. For this purpose, a suitable algorithm determines the spectral peak position and from that the distance of each test point from the objective lens 6 for each measured point. Thus one image can yield the three-dimensional shape of the test object 8 with data in 2000 interpolation points.

If the distance between interpolation points is greater than the required resolution and/or the three-dimensional shape can not be acquired from one viewpoint, the illumination pattern must be shifted accordingly. In the illustrated embodiment, this is achieved by moving the hand-set, whereby the resulting individual images are merged into a total image in a suitable manner.

As a positioning aid and to assist with assigning individual images properly when assembling the overall image, a further camera chip 14 for recording a live image is provided in the embodiment example. For recording a live image, one or several light sources 15 are provided that emit light in a spectral region outside of the wavelength region used for the actual measuring. In this embodiment example, the light sources 15 and the camera chip 14 are integrated into the hand-set. Beam splitting is accomplished by means of a suitable beam splitter 13. The axial position of the camera chip 14 is chosen so that the live image is in focus approximately in the centre of the measurement region.

The mentioned hand-set in this embodiment example comprises a section of the light guides 5 as well as the subsequent components arranged on the object side, i.e. beam splitter 13, camera chip 14, objective lens 6, additional light source 15, as well as beam deflector 7. The evaluation unit comprises the remaining components. The hand-set and the evaluation unit are connected via the light guides. Consequently, the ends on the object side, which are located in the imaging plane(s) of the objective lens, are contained in the hand-set, while the ends on the illumination or detection side are contained in the separate evaluation unit.

Some of the feasible light sources with a broadband spectrum are halogen lamps, xenon lamps, and in particular LEDs, either white-light LEDs or RGB LEDs. The use of LEDs offers the option of a modulated or pulsed or flashed illumination (at a power that is higher than the continuous operation power). This, in combination with a detection process that is synchronized with the light source, allows achieving an efficient stray light suppression.

The use of several light sources is also possible. When using LEDs this can increase the total amount of light. The spatial arrangement of the individual light sources can be adapted to the spatial arrangement of the light guides. Thus each of the individual light sources only illuminates a certain portion of the light guides.

A colour camera can be used as the colour-measuring unit, particularly in measuring tasks where the stray light level is low. Depending on the requirements for measurement accuracy, a one-chip colour camera, a three-chip colour camera, or a colour camera with filter-wheel technology may be used.

The higher the fraction of the measured signal that is contributed by the stray light background, be that by scattering and/or by ambient stray light, the more important it will be to also measure the spectral distribution of the background in order to be able to precisely determine the peak position. This becomes possible if a portion of the light guides 5 is not illuminated and consequently only the returned background light is acquired on the sample side.

In the embodiment illustrated in FIG. 2a, the light guides serving for background determination 16 on the illumination or detection side are all positioned in one line that is not illuminated. On the sample side (FIG. 2b), the light guides 5 for background determination 16 are uniformly distributed among the other light guides.

In order to reduce the background light fraction, it is possible to use for each individual measurement only half of the light guides 5 for the actual measurement, while the other, not illuminated portion is used for measuring the background. Variations in illumination can be effected for example using an LCD modulator or using the variable beam offset of a tilting glass plate. The light guides of one line in any individual measurements will all be used either for distance measuring or background measuring.

The determination of the background can also be accomplished if after a measurement the image plane is shifted by an optical element, e.g. by inserting a glass plate, and the measurement is repeated. This will shift the peak in the spectrum by a fixed value into a different wavelength region. The background can be extensively eliminated by performing suitable computations using the two spectra. The unknown distance can be determined from the peak position of the two spectra.

In addition to the use of individual cylindrical lenses to illuminate the light guides arranged along lines, one can also envision the use of a specially adapted array of (micro-) cylindrical lenses.

If line-shaped foci are generated for coupling-in purposes, then the coupling-in efficiency can be increased by using light guides without a fibre sheath on the coupling-in side, since light guides then can be lined up close to each other without any separation.

To improve the coupling-in efficiency one can also envision the combination of cylindrical lenses with a microlens array or the use of cross-cylindrical lenses, to generate a pattern of individual foci. A corresponding fibre must be positioned for each focus.

In addition to a uniform, square arrangement of the light guide ends on the sample side, other arrangements are also possible. For example, one could envision a rotationally symmetric arrangement, which would offer manufacturing-related advantages. Possible is also a varying density of light guides per surface area, for example to use a higher density of measuring points to compensate for the lower degree of overlap of individual images in the border region. Alternatively, one can envision a measuring point density that decreases in the border region while at the same time one increases the measuring field, in order to be able to better recognize any tilts between offset individual images. Particularly easy to manufacture is a random arrangement of the light guides, whereby the (mean) distance between light guides can be adjusted either by the fibre sheath itself or by randomly admixed blind fibres or other (cylindrical) components. Assignment of the positions of the individual light guides on the sample side to the corresponding spectrum positions on the detector is achieved by calibration using a suitable test body of known geometry.

In order to prevent erroneous light conduction in the fibre sheath, one can use an absorbing material instead of the sheath on the sample side and/or the coupling-in side. If the number of light guides of standard fibre bundles is not adequate, one can also envision the combined use of several standard fibre bundles.

If the diameter or amount of light of an individual light guide is too low, then one can envision the use of several light guides per measuring location.

It is also possible to subdivide the light guides into functional sub-bundles. This for example makes it possible to image the light of the light guides that are only used for background measurements onto a designated camera chip, for example to be able to adjust the camera image amplification separately for the actual distance measurement and the background measurement. Combining this with several light sources then also creates the possibility to subdivide the distance measuring into several spectral regions with respective adapted light sources (LED) and adapted camera, possibly with adapted colour filters.

In order to achieve a reduction of the diameter of the objective lenses and thus a further minimization of the handset while maintaining a nearly unchanged size of the measuring field, one can envision the use of a non-telecentric objective lens instead of an objective lens with telecentric imaging.

Particularly helpful to uncomplicatedly adapting the measuring unit to the particular task or measuring probe can be the implementation of a system of interchangeable chromatic objective lenses. Depending on the object-to-image ratio, the chromatic aberration, and other optical characteristics, this can be used to adapt the measuring unit to the measuring task, for example with respect to size and density of the measuring points, measuring distance, measuring region, and telemetry.

For the purpose of adapting to the respective measuring task one can also use various beam deflectors, for example re-directing mirrors or prisms of various forms and functions. These are arranged on the sample side, downstream of the chromatic objective lens. But a beam deflection can also take place within the objective lens or between the fibre ends and the objective lens.

For the purpose of referencing the distance measurement, one may use a defined backward reflection, for example from the decoupling surface of the deflection prism. For this purpose one for example can perform a measurement without probe prior to each measuring pass, whereby the respective peak position in these spectra can be assigned to the backward reflection. During the actual measurement on the samples, it may be of advantage to subtract each of the respective reference spectra from the measured spectra.

For generating the live image one can also envision integrating a camera chip with its own objective lens in the hand-set, similar to the "chip on the tip" technology used in endoscopy.

In order to have a good view of the measurement location, one desires the live image to exhibit high depth of field. The latter can be improved if one inserts in the joint optical beam path of measurement and live image a dichroic screen that only affects the spectral region of the live image, e.g. preferably in a plane of an aperture diaphragm of the chromatic objective lens. The depth of field now can be increased by reducing the numerical aperture of the objective lens.

If a too high depth of field of the live image greatly complicates controlling the proper measuring distance, one can envision as an additional axial positioning aid a distance indicator that is superimposed onto the live image, whereby the displayed value may be generated from the measured 3D data.

In particular if only a few of the light guides of one or several fibre bundles are used for the measurement, the unused light guides can be used for the live image.

Alternatively one can use an additional fibre bundle for the live image. On the side of the measuring probe, the measuring beam path and the live image beam path are then combined by means of a suitable optical element.

Alternatively a live image with satisfactory resolution may be generated without an additional camera chip, namely from the signal values of the measuring image and by combination of several individual images. This can for example be accomplished by using the respective peak amplitude in each measuring point spectrum or by way of integration of all values of each spectrum to form a respective brightness value.

Alternatively, on the detection side a portion of the measuring light is imaged directly onto a further camera chip via a further separating mirror, without any spectral dispersion. A live image of higher resolution can be generated from several individual images by proper computational processes. Using the 3D data may improve the results of the computational results using the individual images. Depending on the structure of the test body, the quality of the individual image may be improved either by using an additional narrow-band light source or by using only a portion of the spectral range of the measuring light for the live image detection. The spectral region may be selected by using a dichroic separating mirror.

The invention claimed is:

1. A method for measuring the shape of at least a section of an object (8), in particular of a semi-transparent object such as at least a section of a tooth, using at least one light source to generate light with preferably a broad-band spectrum, a device to generate a multi-focus illumination pattern, an objective lens with high chromatic aberration to image the foci of the illumination pattern onto the object, and a detector unit to determine the wavelength spectra of the foci imaged confocally onto the object by the objective lens, whereby for each focus the spectral peak position of each focus is determined from the corresponding wavelength spectrum, from which the spatial extent of the object along the direction of the imaging beam (z coordinate) is computed, whereby the multi-focal illumination pattern is generated by light guides that are arranged between the light source and the objective lens with high chromatic aberration, whereby the objective lens images the ends of the light guides on the objective side onto the object and images light returned by the object onto the ends of the light guides on the object side, and whereby returned light that is conducted through the light guides is directed onto the detector device, characterized in that one creates an arrangement of the ends of the light guides on the object side that is different from the arrangement of the ends of the light guides on the illumination or detection side so that one obtains a measuring point distribution on the object side that is independent of the distribution of microlenses or pinholes on the illumination or detection side.

2. The method of claim 1,
characterized in that
an arrangement of light guides on the illumination or detection side is chosen to ensure an efficient coupling-in of light from the at least one light source on the one hand and an efficient spatial utilization of the detector device on the other.

3. The method of claim 1,
characterized in that
an arrangement of light guides on the object side is chosen to ensure that in combination with a subsequent superposition of individual images, it ensures an optimum distribution of measuring points on the object.

4. The method of claim 1,
characterized in that
the illumination pattern on the object side is shifted for the recording of individual images, whereby the resulting individual images are merged into an overall image.

5. The method of claim 1,
characterized in that
the light guides on the illumination or detection side are arranged in rows or lines, whereby the light guides preferably are twisted in order to obtain a uniform distribution of light guides on the sample side.

6. The method of claim 1,
characterized in that
calibration is used to assign the positions of the individual light guides on the object or sample side to the ends of the light guides on the illumination side.

7. The method of claim 1,
characterized in that
the returned light for each light guide is dispersed along a line.

8. The method of claim 1,
characterized in that
the light dispersed-along a line is directed onto a camera chip.

9. The method of claim 1,
characterized in that
light exiting from the light guide is laterally dispersed using a dispersive device.

10. The method of claim 1,
characterized in that
the detector device comprises a pixel surface of a chip, such as a CCD sensor, which detects the wavelength spectra, that at least one of the pixel surface and the dispersive device is inclined with respect to the plane defined by the ends of the light guides on the illumination or detection side in such a way that the radiation emerging from the light guides is incident upon the pixel surface without overlap.

11. The method of claim 1,
characterized in that
the light is focused along lines on the ends of the light guides on the illumination or detection side.

12. The method of claim 1,
characterized in that
cylindrical lenses are used to focus the light in lines.

13. The method of claim 1,
characterized in that
a beam of rays that satisfies a confocality condition and passes through a light guide is used to determine a first spectrum, that in the beam path between the objective lens and the light guide is arranged an optical element that changes the beam path, that a second spectrum is determined from the beam of rays with modified beam path, and that the spectra are subtracted from each other, and that the wavelength of the beam of rays is determined from the resulting identical peaks with opposite sign.

14. A measuring arrangement for the three-dimensional measuring of at least part of an object, in particular of a semi-transparent object, such as a tooth or section thereof, comprising a light source with a continuous in particular wide-band spectrum, a device to generate a multi-focus illumination pattern, an objective lens with high chromatic aberration to image foci of the illumination pattern onto the object, a detector unit, such as a camera chip, to determine the wavelength spectra of the foci imaged onto the object by the objective lens, as well as a spectrum-dispersing device, onto which light returning from the object can be imaged, whereby arranged between the light source and the objective lens are light guides, which generate the illumination pattern and possess ends on the object side that are arranged in an imaging plane or range of imaging planes of the objective lens, whereby between the ends of the light guides on the illumination side and the detector device is arranged a deviating device for the light emerging from the light guide and the light returning from the object,
characterized in that
the ends of the light guides on the object side are arranged in a manner so that a measuring point distribution can be imaged on the object side that is independent of the distribution of microlenses or pinholes on the illumination or detection side.

15. The measuring arrangement of claim 14, characterized in that
the ends of the light guides on the illumination or detections side are arranged to ensure an efficient coupling-in of light from the at least one light source on the one hand, and an efficient spatial utilization of the detector device on the other, and that the ends of the light guides on the object side are arranged to ensure an optimum distribution of measuring points on the object.

16. The measuring arrangement of claim 14,
characterized in that
the measuring arrangement comprises several light sources, whereby a spatial arrangement of the individual light sources is adapted to the spatial arrangement of the light guides.

17. The measuring arrangement of claim 14,
characterized in that
the light guides on the illumination or detection side are arranged in rows or lines.

18. The measuring arrangement of claim 14,
characterized in that
the light guides are combined into a bundle that consists of sub-bundles, whereby one sub-bundle can be used to perform a background measurement.

19. The measuring arrangement of claim 14,
characterized in that
the light guides for background determination on the illumination or detection side are all arranged along one line that is not illuminated, and that the light guides for background determination on the sample side are distributed uniformly among the other light guides.

20. The measuring arrangement of claim 14,
characterized in that
the ends of the light guides on the sample side are arranged uniformly, in a square pattern.

21. The measuring arrangement of claim 14,
characterized in that
the light guides are arranged randomly, whereby a (mean) distance between light guides can be set either using the fibre sheath itself or using randomly admixed blind fibres or other (cylindrical) components.

22. The measuring arrangement of claim 14,
characterized in that
an assignment of the positions of the individual light guides on the sample side to the corresponding spectrum position on the detector device can be performed by calibration on a suitable test body of known geometry.

23. The measuring arrangement of claim 14,
characterized in that
the light guide ends are arranged in a rotationally symmetrical fashion.

24. The measuring arrangement of claim 14,
characterized in that
light can be imaged onto the ends of the light guides on the illumination side via cylindrical lenses.

25. The measuring arrangement of claim 14,
characterized in that
light focussed along lines can be imaged onto the ends of the light guides on the illumination side.

26. The measuring arrangement of claim 14,
characterized in that
the measuring arrangement consists of a hand-set and a measuring unit that can be located at a distance thereto and that the two are connected via the light guides.

27. The measuring arrangement of claim 14,
characterized in that
the hand-set comprises the ends of the light guides on the object side, the objective lens with high chromatic aberration, as well as at least one deviating device.

28. The measuring arrangement of claim 14,
characterized in that
the measuring arrangement comprises an interchangeable chromatic objective lens.

29. The measuring arrangement of claim 14,
characterized in that
the objective lens forms a telecentric image.

30. The measuring arrangement of claim 14,
characterized in that
the light guides on the coupling-in side are free of a fibre sheath.

31. The measuring arrangement of claim 14,
characterized in that
the radiation can be imaged onto the light guide ends via cylindrical lenses with microlens array or cross-cylindrical lenses.

32. The measuring arrangement of claim 14,
characterized in that
at least on the object side, the light guide ends are combined into a bundle with preferably a square cross section.

33. The measuring arrangement of claim 14, characterized in that the light guides are combined into a bundle that consists of sub-bundles, whereby one sub-bundle can be used to perform a background measurement.

34. The measuring arrangement of claim 14, characterized in that the measuring arrangement, in particular the hand-set, comprises a camera chip to generate a live image.

35. The measuring arrangement of claim 14, characterized in that the light source is a halogen lamp, a xenon lamp, or one or several LEDs.

36. The measuring arrangement of claim 14, characterized in that the light source is made up of white-light LEDs or RGB LEDs.

37. The measuring arrangement of claim 14, characterized in that the LEDs emit modulated or pulsed radiation.

38. The measuring arrangement of claim 14, characterized in that the LEDs illuminated the light guide ends in a flashed mode.

39. The measuring arrangement of claim 14, characterized in that the detector device comprises a 1-chip colour camera, a 3-chip colour camera, or a colour camera with filter-wheel technology.

40. The measuring arrangement of claim 14, characterized in that, the light guides are twisted so that the light guides on the sample side exhibit a uniform distribution.

41. The measuring arrangement of claim 14, characterized in that the ends of the light guides on the sample side are arranged uniformly, in a rotationally symmetric pattern.

42. The measuring arrangement of claim 14, characterized in that the light guides per surface area exhibit a varying density.

43. The measuring arrangement of claim 14, characterized in that the measuring point density decreases in a border region, with a simultaneous increase in the measuring field size.

* * * * *